United States Patent [19]

Kulprathipanja et al.

[11] 4,455,444

[45] * Jun. 19, 1984

[54] LOW TEMPERATURE PROCESS FOR SEPARATING HYDROCARBONS

[75] Inventors: Santi Kulprathipanja, Hoffman Estates; Richard W. Neuzil, Downers Grove, both of Ill.

[73] Assignee: Uop Inc., Des Plaines, Ill.

[*] Notice: The portion of the term of this patent subsequent to Jan. 4, 2000 has been disclaimed.

[21] Appl. No.: 441,142

[22] Filed: Nov. 12, 1982

Related U.S. Application Data

[63] Continuation-in-part of Ser. No. 288,570, Jul. 30, 1981, Pat. No. 4,367,364.

[51] Int. Cl.³ .............................................. C07C 7/12
[52] U.S. Cl. ............................... 585/826; 208/310 Z; 585/827; 585/828
[58] Field of Search ....................... 585/826, 827, 828; 208/310 Z, 310 R

[56] References Cited

U.S. PATENT DOCUMENTS

| | | | |
|---|---|---|---|
| 2,957,927 | 10/1960 | Broughton et al. | 585/826 |
| 3,239,455 | 3/1966 | Lickus et al. | 208/310 R |
| 3,405,057 | 10/1968 | Neuzil | 208/310 Z |
| 4,000,059 | 12/1976 | Wanless | 208/310 Z |
| 4,006,197 | 2/1977 | Bieser | 208/310 Z |
| 4,061,724 | 12/1977 | Grose et al. | 423/335 |
| 4,104,294 | 8/1978 | Grose et al. | 260/448 C |
| 4,309,281 | 1/1982 | Dessau | 208/310 Z |
| 4,367,364 | 1/1983 | Kulprathipanja | 585/826 |

Primary Examiner—Delbert E. Gantz
Assistant Examiner—A. Pal
Attorney, Agent, or Firm—James R. Hoatson, Jr.; Louis A. Morris; William H. Page, II

[57] ABSTRACT

A process for separating a normal paraffin hydrocarbon from a mixture of the same with a cyclic and/or branched chain paraffin hydrocarbon. The process comprises contacting the mixture at a temperature of from about 120° C. to about 140° C. with a zeolite free molecular sieve comprising silicalite. The normal paraffin hydrocarbon is selectively retained and will preferably be recovered from the molecular sieve by displacement with a displacement material.

11 Claims, 5 Drawing Figures

LOW TEMPERATURE PROCESS FOR SEPARATING HYDROCARBONS

CROSS REFERENCE TO RELATED APPLICATION

This application is a continuation-in-part of our prior co-pending application U.S. Ser. No. 288,570 filed July 30, 1981 and issued on Jan. 4, 1983 as U.S. Pat. No. 4,367,364, incorporated herein by reference.

BACKGROUND OF THE INVENTION

The field of art to which this invention pertains is hydrocarbon separation. Specifically, this invention relates to a process which utilizes a crystalline silica composition as a molecular sieve and a displacement material to separate a normal hydrocarbon from a feed mixture of the same with a branched chain or cyclic hydrocarbon at a relatively low temperature.

DESCRIPTION OF THE PRIOR ART

There is an abundance of prior art in the separation field, especially art relating to countercurrent fixed bed type operations, which deal with the separation of normal paraffins from other classes of hydrocarbons using a solid adsorbent. Examples of such art are U.S. Pat. Nos. 2,957,927 to Broughton et al; 3,239,455 to Lickus et al; 3,405,057 to Neuzil et al; 4,000,059 to Wanless; 4,006,197 to Bieser; and 4,309,281 to Dessau. The most common adsorbent used throughout the prior art processes for the above separations are the crystalline aluminosilicates, the best known of which are the zeolites. The crystalline aluminosilicates function as "molecular sieves", that is, they contain pores having cross-sectional diameters which will accept certain molecules in a mixture of molecules of specific size and shape, i.e. normal paraffins; while rejecting others, i.e. branched chain and cyclic, thereby separating the accepted molecules from the mixture.

A new crystalline silica molecular sieve type adsorbent material known as "silicalite" has recently been invented. Silicalite is disclosed and claimed in U.S. Pat. Nos. 4,061,724 and 4,104,294 to Grose et al. The separation process utilizing silicalite contemplated by the Grose et al patents comprises, in general terms, the separation of an organic compound from an aqueous solution. The organic molecules separated from their organic solutions in the separations exemplified in Grose et al (4,061,724) are n-butanol, methyl cellosolve, methanol and phenol.

The present invention relates to a process for separating a normal hydrocarbon from a mixture of the same with a cyclic and/or branched chain hydrocarbon using silicalite rather than the adsorbents or molecular sieves known to the art for that separation. It has been discovered that silicalite is a molecular sieve particularly suitable for such process and most particularly suitable when the process is carried out at a temperature of from about 120° C. to about 140° C.

SUMMARY OF THE INVENTION

In brief summary the invention is, in one embodiment, a process for separating a normal hydrocarbon from a mixture of the same with a cyclic hydrocarbon other than benzene, or a branched chain hydrocarbon. The process comprises contacting the mixture at separation conditions including a temperature of from about 120° C. to about 140° C. with a zeolite-free molecular sieve comprising silicalite to effect the selective retention of the normal hydrocarbon by the molecular sieve.

In another embodiment the present invention is a process for separating a normal hydrocarbon from a mixture of the same with a cyclic hydrocarbon other than benzene, or a branched chain hydrocarbon. The process employs a molecular sieve comprising silicalite. The process comprises the steps of: (a) maintaining net fluid flow through a column of the molecular sieve in a single direction, which column contains at least three zones having separate operational functions occurring therein and being serially interconnected with the terminal zones of the column connected to provide a continuous connection of the zones; (b) maintaining a retention zone in the column, the zone defined by the molecular sieve located between a feed input stream at an upstream boundary of the zone and a raffinate output stream at a downstream boundary of the zone; (c) maintaining a purification zone immediately upstream from the retention zone, the purification zone defined by the molecular sieve located between an extract output stream at an upstream boundary of the purification zone and the feed input stream at a downstream boundary of the purification zone; (d) maintaining a displacement zone immediately upstream from the purification zone, the displacement zone defined by the molecular sieve located between a displacement fluid input stream at an upstream boundary of the zone and the extract output stream at a downstream boundary of the zone; (e) passing the feed mixture into the retention zone at separation conditions to effect the selective retention of the normal hydrocarbon by the molecular sieve in the retention zone and withdrawing a raffinate output stream from the retention zone; (f) passing a displacement fluid into the displacement zone at displacement conditions to effect the displacement of the normal hydrocarbon from the molecular sieve in the displacement zone; (g) withdrawinq an extract output stream comprising the normal hydrocarbon and displacement fluid from the displacement zone; (h) withdrawing a raffinate output stream comprising the branched chain and/or cyclic hydrocarbon from the displacement zone; and (i) periodically advancing through the column of molecular sieve in a downstream direction with respect to fluid flow in the retention zone, the feed input stream, raffinate output stream, displacement fluid input stream, and extract output stream to effect the shifting of zones through the molecular sieve and the production of extract output and raffinate output streams.

Other embodiments of the present invention encompass details about feed mixtures, molecular sieves, displacement fluids and operatinq conditions all of which are hereinafter disclosed in the following discussion of each of the facets of the present invention.

DESCRIPTION OF THE INVENTION

In order to gain a better understanding of the process of this invention, the following definitions of terms that are used throughout this specification are given.

The term "feed stream" indicates a stream in the process through which feed material passes to the molecular sieve. A feed material comprises one or more extract components and one or more raffinate components. An "extract component" is a compound or type of compound that is more selectively retained by the molecular sieve while a "raffinate component" is a compound or type of compound that is less selectively retained. In this process normal hydrocarbons from the feed stream are extract components while feed stream branched chain and cyclic hydrocarbons are raffinate components. Usually the term "extract component" as used herein refers to a more selectively retained compound or type of compound which is to be the desired product, such as normal hydrocarbons in this process. The term "displacement fluid" shall mean generally a material capable of displacing an extract component. The term "displacement fluid" or "displacement fluid input stream" indicates the stream through which displacement fluid passes to the molecular sieve. The term "raffinate output stream" means a stream through which most of the raffinate components are removed from the molecular sieve. The composition of the raffinate stream can vary from about 100% displacement fluid to essentially 100% raffinate components. The term "extract stream" or "extract output stream" shall mean a stream through which an extract material which has been displaced by a displacement fluid is removed from the molecular sieve. The composition of the extract stream can also vary from about 100% displacement fluid to essentially 100% extract components.

Although it is possible by the process of this invention to produce high purity (99+%) normal hydrocarbons at hiqh recoveries (90% or higher), it will be appreciated that an extract component is never completely retained by the molecular sieve, nor is a raffinate component completely non-retained by the molecular sieve. Therefore, small amounts of a raffinate component can appear in the extract stream and, likewise, small amounts of an extract component can appear in the raffinate stream. The extract and raffinate streams then are further distinguished from each other and from the feed mixture by the ratio of the concentrations of an extract component and a raffinate component appearing in the particular stream. More specifically, the ratio of the concentration of the retained normal hydrocarbons to that of the non-retained components will be lowest in the raffinate stream, next highest in the feed mixture, and the highest in the extract stream. Likewise, the ratio of the concentration of the non-retained components to that of the retained normal hydrocarbons will be highest in the raffinate stream, next highest in the feed mixture, and the lowest in the extract stream.

The term "selective pore volume" of the molecular sieve is defined as the volume of the molecular sieve which selectively retains extract components from the feed stock. The term "non-selective void volume" of the molecular sieve is the volume of the molecular sieve which does not selectively retain extract components from the feed stock. This volume includes the cavities of the molecular sieve which are capable of retaining raffinate components and the interstitial void spaces between molecular sieve particles. The selective pore volume and the non-selective void volume are generally expressed in volumetric quantities and are of importance in determining the proper flow rates of fluid required to be passed into an operational zone for efficient operations to take place for a given quantity of molecular sieve.

When molecular sieve "passes" into an operational zone (hereinafter defined and described) its non-selective void volume together with its selective pore volume carries fluid into that zone. The non-selective void volume is utilized in determining the amount of fluid which should pass into the same zone in a countercurrent direction to the molecular sieve to displace the fluid present in the non-selective void volume. If the fluid flow rate passing into a zone is smaller than the non-selective void volume rate of molecular sieve material passing into that zone, there is a net entrainment of liquid into the zone by the molecular sieve. Since this net entrainment is a fluid present in non-selective void volume of the molecular sieve, it in most instances comprises less selectively retained feed components.

Feed stocks which can be used in the process of this invention will be hydrocarbon fractions having a carbon number range of from about two carbon atoms per molecule up to 17 carbon atoms per molecule. Typically, the carbon number range of the hydrocarbon fractions will be rather narrow, such as from about three to about ten carbon numbers. A $C_{10}$–$C_{15}$ kerosine fraction is a typical feed stream. Feed streams will usually contain normal paraffins, isoparaffins and cyclohydrocarbons, including aromatics having greater than six carbon atoms per molecule, in varying concentrations but little or no olefins. Depending on the type of crude from which the hydrocarbon fraction is derived and the carbon number range of the fraction, the normal paraffin concentration will typically range from about 15 to about 60 vol.% of the feed and the aromatic concentration from about 10 to about 30 vol.% of the feed. There may be more unusual feed streams which have aromatic concentrations of only about 2 to about 4 vol.% of the feed stream. Since the feed aromatics other than benzene, like the alkylbenzenes, cannot enter the pores of molecular sieve used in this process because their cross-sectional diameter is too great, almost all of the aromatics appear in the raffinate stream. The feed aromatics can include monocyclic aromatics such as alkylbenzenes; indanes or alkylindanes; and bicyclic aromatics including naphthalenes, biphenyls, or the acenaphthenes. Certain para-substituted di-alkyl benzenes may also be unsuitable as feed components because of a too small maximum cross-sectional diameter which enable the molecule to enter the silicalite pores.

Displacement fluids or desorbent materials used in various prior art adsorptive or molecular sieve separation processes vary depending upon such factors as the type of operation employed. In the swing bed system in which the selectively retained feed component is removed from the molecular sieve by a purge stream, displacement fluid selection is not as critical and displacement fluid comprising gaseous hydrocarbons such as methane, ethane, etc., or other types of gases such as nitrogen or hydrogen may be used at elevated temperatures or reduced pressures or both to effectively purge the retained feed component from the molecular sieve. However, in molecular sieve separation processes which are generally operated continuously at substantially constant pressures and temperatures to ensure liquid phase, the displacement fluid must be judiciously selected to satisfy many criteria. First, the displacement fluid should displace an extract component from the molecular sieve with reasonable mass flow rates and without itself being too strongly retained. Secondly, displacement fluid must be compatible with the particular molecular sieve and the particular feed mixture. More specifically, they must not reduce or destroy the critical ability of the molecular sieve to retain an extract component and reject a raffinate component. Displacement fluids should additionally be substances which are easily separable from the feed mixture that is passed into the process. Both the raffinate stream and the extract stream are removed from the molecular sieve in admixture with displacement fluid and without a method of separating at least a portion of the displacement fluid, the purity of the extract product and the raffinate product would not be very high, nor would the displacement fluid be available for reuse in the process. It is therefore contemplated that any displacement fluid used in this process will preferably have a substantially different average boiling point than that of the feed mixture to allow separation of at least a portion of displacement fluid from feed components in the extract and raffinate streams by simple fractional distillation thereby permitting reuse of displacement fluid in the process. The term "substantially different" as used herein shall mean that the difference between the average boiling points between the displacement fluid and the feed mixture shall be at least about 5° C. The boiling range of the displacement fluid may be higher or lower than that of the feed mixture. Finally, displacement fluid should also be materials which are readily available and therefore reasonable in cost. In the preferred isothermal, isobaric, liquid-phase operation of the process of this invention, it has been found that displacement fluids comprising a normal hydrocarbon having a boiling point substantially different from that of the feed mixture meet these requirements and is particularly effective. A particularly preferred mixture for displacement material is iso-octane and a normal olefin such as hexene-1. The iso-octane functions as a carrier and diluent for the olefin which effects the actual displacement, and also serves to flush the void spaces of the molecular sieve.

The molecular sieve to be used in the process of this invention comprises the silicalite of Grose et al as previously mentioned. Silicalite is a hydrophobic crystalline silica molecular sieve. Due to its aluminum free structure, silicalite does not show ion-exchange behavior, and is hydrophobic and organophilic. Silicalite thus comprises a molecular sieve but not the hydrated aluminum or calcium silicate comprising a zeolite. Silicalite is uniquely suitable for the separation process of this invention for the presumed reason that its pores are of a size and shape (about 6 angstrom units in diameter) that enable the silicalite to function as a molecular sieve, i.e. accept the molecules of $C_6$ normal paraffins into its channels or internal structure, while rejecting the molecules of $C_6$ hydrocarbons of other structural classes. A more detailed discussion of silicalite may be found in the article "Silicalite, A New Hydrophobic Crystalline Silica Molecular Sieve"; *Nature,* Vol. 271, Feb. 9, 1978, incorporated herein by reference.

Commercially available molecular sieves heretofore used in the separation of the present invention have some entrance diameters less than 6 angstroms, examples of which are chabazite, Type A (both sodium and calcium forms), faujasite, mordenite, etc. A serious problem with these adsorbents is the low exchange rate for displacement of feed straight chain hydrocarbons with displacement fluid molecules and thus the long and inefficient cycle times required to effect displacement. The discovery leading to the present invention is that silicalite, which has some entrance diameters of 6 angstroms, does not exhibit such low exchange rate.

The molecular sieve may be employed in the form of a dense compact fixed bed which is alternatively contacted with the feed mixture and displacement fluid materials. In the simplest embodiment of the invention the molecular sieve is employed in the form of a single static bed in which case the process is only semi-continuous. In another embodiment a set of two or more static beds may be employed in fixed bed contacting with appropriate valving so that the feed mixture is passed through one or more molecular sieve beds while the displacement fluid materials can be passed through one or more of the other beds in the set. The flow of feed mixture and displacement fluid materials may be either up or down through the molecular sieve. Any of the conventional apparatus employed in static bed fluid-solid contacting may be used. The particles of silicalite molecular sieve will preferably have a particle size range of about 16–60 mesh (Standard U.S. Mesh).

Countercurrent moving bed or simulated moving bed countercurrent flow systems have a much greater separation efficiency than fixed molecular sieve bed systems and are therefore preferred. In the moving bed or simulated moving bed processes the retention and displacement operations are continuously taking place which allows both continuous production of an extract and a raffinate stream and the continual use of feed and displacement fluid streams. One preferred embodiment of this process utilizes what is known in the art as the simulated moving bed countercurrent flow system. The operating principles and sequence of such flow system are described in U.S. Pat. No. 2,985,589 incorporated herein by reference. In such a system it is the progressive movement of multiple liquid access points down a molecular sieve chamber that simulates the upward movement of molecular sieve contained in the chamber. Only four of the access lines are active at any one time: the feed input stream, displacement fluid inlet stream, raffinate outlet stream, and extract outlet stream access lines. Coincident with this simulated upward movement of the solid molecular sieve is the movement of the liquid occupying the void volume of the packed bed of molecular sieve. So that countercurrent contact is maintained, a liquid flow down the molecular sieve chamber may be provided by a pump. As an active liquid access point moves through a cycle, that is, from the top of the chamber to the bottom, the chamber circulation pump moves through different zones which require different flow rates. A programmed flow controller may be provided to set and regulate these flow rates.

The active liquid access points effectively divide the molecular sieve chamber into separate zones, each of which has a different function. In this embodiment of the process it is generally necessary that three separate operational zones be present in order for the process to take place although in some instances an optional fourth zone may be used.

The retention zone, zone 1, is defined as the molecular sieve located between the feed inlet stream and the raffinate outlet stream. In this zone, the feedstock contacts the molecular sieve, an extract component is retained, and a raffinate stream is withdrawn. Since the general flow through zone 1 is from the feed stream which passes into the zone to the raffinate stream which passes out of the zone, the flow in this zone is considered to be a downstream direction when proceeding from the feed inlet to the raffinate outlet streams.

Immediately upstream with respect to fluid flow in zone 1 is the purification zone, zone 2. The purification zone is defined as the molecular sieve between the extract outlet stream and the feed inlet stream. The basic operations taking place in zone 2 are the displacement from the non-selective void volume of the molecular sieve of any raffinate material carried into zone 2 by the shifting of molecular sieve into this zone and the displacement of any raffinate material retained within the selective pore volume of the molecular sieve. Purification is achieved by passing a portion of extract stream material leaving zone 3 into zone 2 at zone 2's upstream boundary, the extract outlet stream to effect the displacement of raffinate material. The flow of material in zone 2 is in a downstream direction from the extract outlet stream to the feed inlet stream.

Immediately upstream of zone 2 with respect to the fluid flowing in zone 2 is the displacement zone or zone 3. The displacement zone is defined as the molecular sieve between the displacement fluid inlet and the extract outlet stream. The function of the displacement zone is to allow a displacement fluid which passes into this zone to displace the extract component which was retained in the molecular sieve during a previous contact with feed in zone 1 in a prior cycle of operation. The flow of fluid in zone 3 is essentially in the same direction as that of zones 1 and 2.

In some instances an optional buffer zone, zone 4, may be utilized. This zone, defined as the molecular sieve between the raffinate outlet stream and the displacement fluid inlet stream, if used, is located immediately upstream with respect to the fluid flow to zone 3. Zone 4 would be utilized to conserve the amount of displacement fluid utilized in the displacement step since a portion of the raffinate stream which is removed from zone 1 can be passed into zone 4 to displace displacement fluid present in that zone out of the zone into the displacement zone. Zone 4 will contain enough displacement fluid so that raffinate material present in the raffinate stream passing out of zone 1 and into zone 4 can be prevented from passing into zone 3 thereby contaminating extract stream removed from zone 3. In the instances in which the fourth operational zone is not utilized the raffinate stream passed from zone 1 to zone 4 must be carefully monitored in order that the flow directly from zone 1 to zone 3 can be stopped when there is an appreciable quantity of raffinate material present in the raffinate stream passing from zone 1 into zone 3 so that the extract outlet stream is not contaminated.

A cyclic advancement of the input and output streams through the fixed bed of molecular sieve can be accomplished by utilizing a manifold system in which the valves in the manifold are operated in a sequential manner to effect the shifting of the input and output streams thereby allowing a flow of fluid with respect to solid molecular sieve in a countercurrent manner. Another mode of operation which can effect the countercurrent flow of solid molecular sieve with respect to fluid involves the use of a rotating disc valve in which the input and output streams are connected to the valve and the lines through which feed input, extract output, displacement fluid input and raffinate output streams pass are advanced in the same direction through the molecular sieve bed. Both the manifold arrangement and disc valve are known in the art. Specifically rotary disc valves which can be utilized in this operation can be found in U.S. Pat. Nos. 3,040,777 and 3,422,848, incorporated herein by reference. Both of the aforementioned patents disclose a rotary type connection valve in which the suitable advancement of the various input and output streams from fixed sources can be achieved without difficulty.

In many instances, one operational zone will contain a much larger quantity of molecular sieve than some other operational zone. For instance, in some operations the buffer zone can contain a minor amount of molecular sieve as compared to the molecular sieve required for the retention and purification zones. It can also be seen that in instances in which displacement fluid is used which can easily displace extract material from the molecular sieve that a relatively small amount of molecular sieve will be needed in a displacement zone as compared to the molecular sieve needed in the buffer zone or retention zone or purification zone or all of them. Since it is not required that the molecular sieve be located in a single column, the use of multiple chambers or a series of columns is within the scope of the invention.

It is not necessary that all of the input or output streams be simultaneously used, and in fact, in many instances some of the streams can be shut off while others effect an input or output of material. The apparatus which can be utilized to effect the process of this invention can also contain a series of individual beds connected by connecting conduits upon which are placed input or output taps to which the various input or output streams can be attached and alternately and periodically shifted to effect continuous operation. In some instances, the connecting conduits can be connected to transfer taps which during the normal operations do not function as a conduit through which material passes into or out of the process.

It is contemplated that at least a portion of the extract output stream will pass into a separation means wherein at least a portion of the displacement fluid can be separated to produce an extract product containing a reduced concentration of displacement fluid. Preferably, but not necessary to the operation of the process, at least a portion of the raffinate output stream will also be passed to a separation means wherein at least a portion of the displacement fluid can be separated to produce a displacement fluid stream which can be reused in the process and a raffinate product containing a reduced concentration of displacement fluid. The separation means will typically be a fractionation column, the design and operation of which is well known to the separation art.

Reference can be made to D. B. Broughton U.S. Pat. No. 2,985,589, and to a paper entitled "Continuous Adsorptive Processing—A New Separation Technique" by D. B. Broughton presented at the 34th Annual Meeting of the Society of Chemical Engineers at Tokyo, Japan on Apr. 2, 1969, both references incorporated herein by reference, for further explanation of the simulated moving bed countercurrent process flow scheme.

Although both liquid and vapor phase operations can be used in many adsorptive type separation processes, liquid-phase operation is preferred for this process because of the lower temperature requirements and because of the higher yields of extract product that can be obtained with liquid-phase operation over those obtained with vapor-phase operation. Retention conditions will therefore include a pressure sufficient to maintain liquid phase. Displacement conditions will include the same range of temperatures and pressures as used for retention conditions.

The size of the units which can utilize the process of this invention can vary anywhere from those of pilot-plant scale (see for example U.S. Pat. No. 3,706,812) to those of commercial scale and can range in flow rates from as little as a few cc an hour up to many thousands of gallons per hour.

A dynamic testing apparatus is employed to test various molecular sieves with a particular feed mixture and displacement material to measure the molecular sieve characteristics of retention capacity and exchange rate. The apparatus consists of a molecular sieve chamber of approximately 70 cc volume having inlet and outlet portions at opposite ends of the chamber. The chamber is contained within a temperature control means and, in addition, pressure control equipment is used to operate the chamber at a constant predetermined pressure. Quantitative and qualitative analytical equipment such as refractometers, polarimeters and chromatographs can be attached to the outlet line of the chamber and used to detect quantitatively or determine qualitatively one or more components in the effluent stream leaving the molecular sieve chamber. A pulse test, performed using this apparatus and the following general procedure, is used to determine selectivities and other data for various molecular sieve systems. The molecular sieve is filled to equilibrium with a particular displacement material by passing the displacement material through the molecular sieve chamber. At a convenient time, a pulse of feed containing known concentrations of a particular extract component or of a raffinate component or both, all diluted in displacement fluid, is injected for a duration of several minutes. Displacement fluid flow is resumed, and the extract component or the raffinate component (or both) are eluted as in a liquid-solid chromatographic operation. The effluent can be analyzed on-stream or alternatively, effluent samples can be collected periodically and later analyzed separately by analytical equipment and traces of the envelopes or corresponding component peaks developed.

From information derived from the test, molecular sieve performance can be rated in terms of void volume, retention volume for an extract or a raffinate component and the rate of displacement of an extract component by the displacement fluid. The retention volume of an extract or a raffinate component may be characterized by the distance between the center of the peak envelope of an extract or a raffinate component and the peak envelope of the tracer component or some other known reference point. It is expressed in terms of the volume in cubic centimeters of displacement fluid pumped during this time interval represented by the distance between the peak envelopes. The rate of exchange of an extract component with the displacement fluid can generally be characterized by the width of the peak envelopes at half intensity. The narrower the peak width, the faster the displacement rate. The displacement rate can also be characterized by the distance between the center of the tracer peak envelope and the disappearance of an extract component which has just been displaced. This distance is again the volume of displacement fluid pumped during this time interval.

The following example is presented to further illustrate the process of this invention but it is not intended to limit the invention to the operating conditions nor the materials disclosed therein.

EXAMPLE

Figure 1:
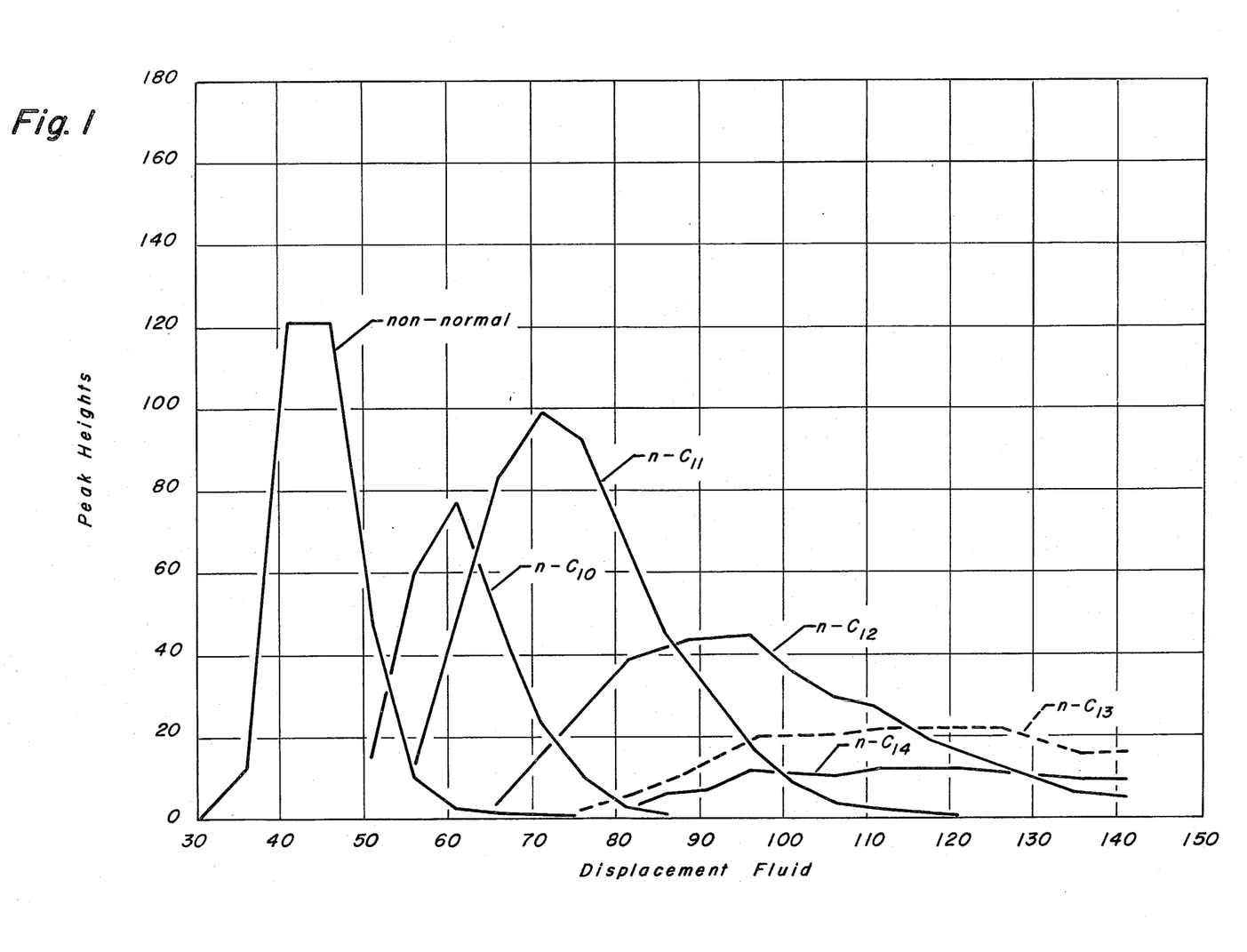
Figure 2:
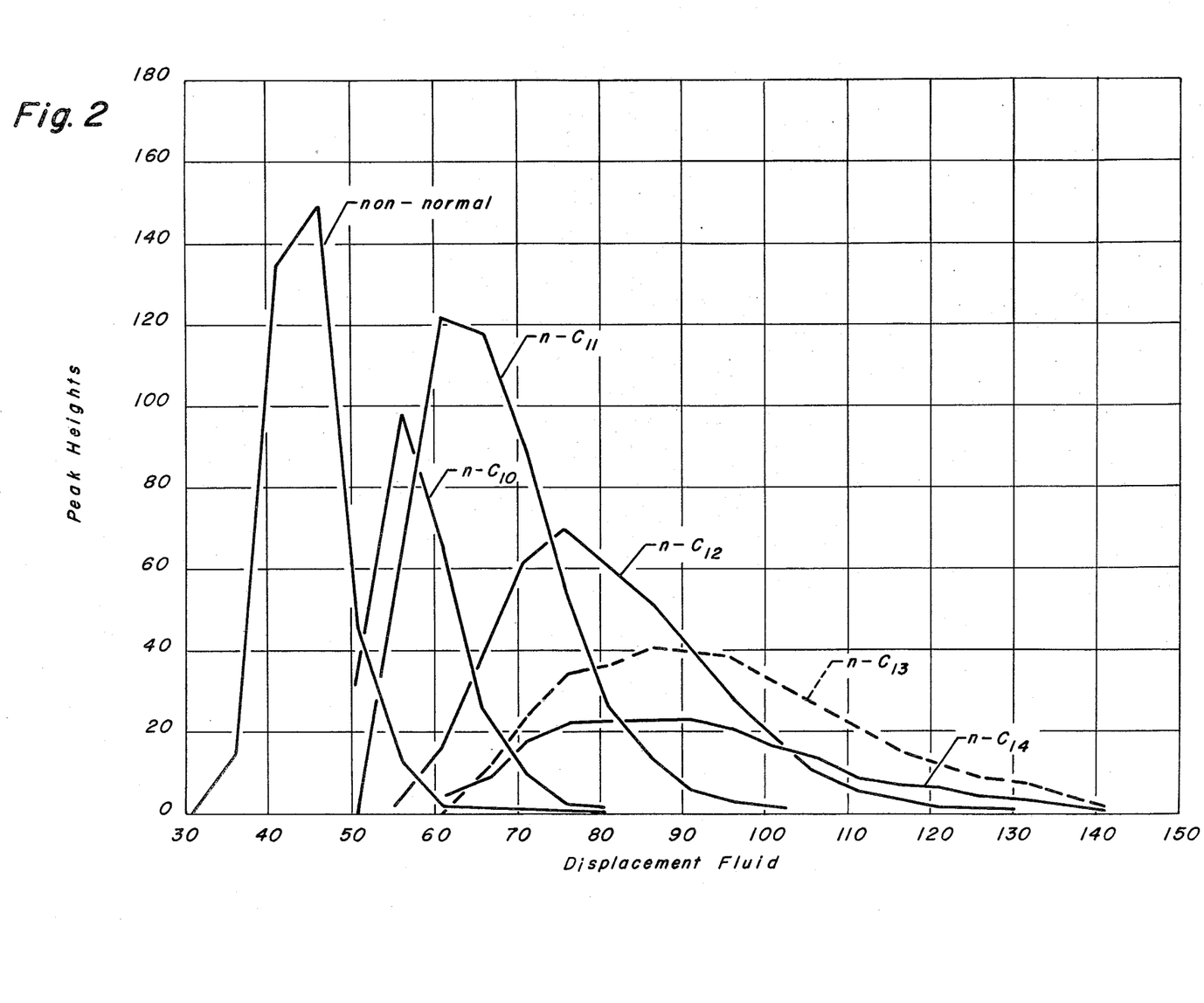
Figure 3:
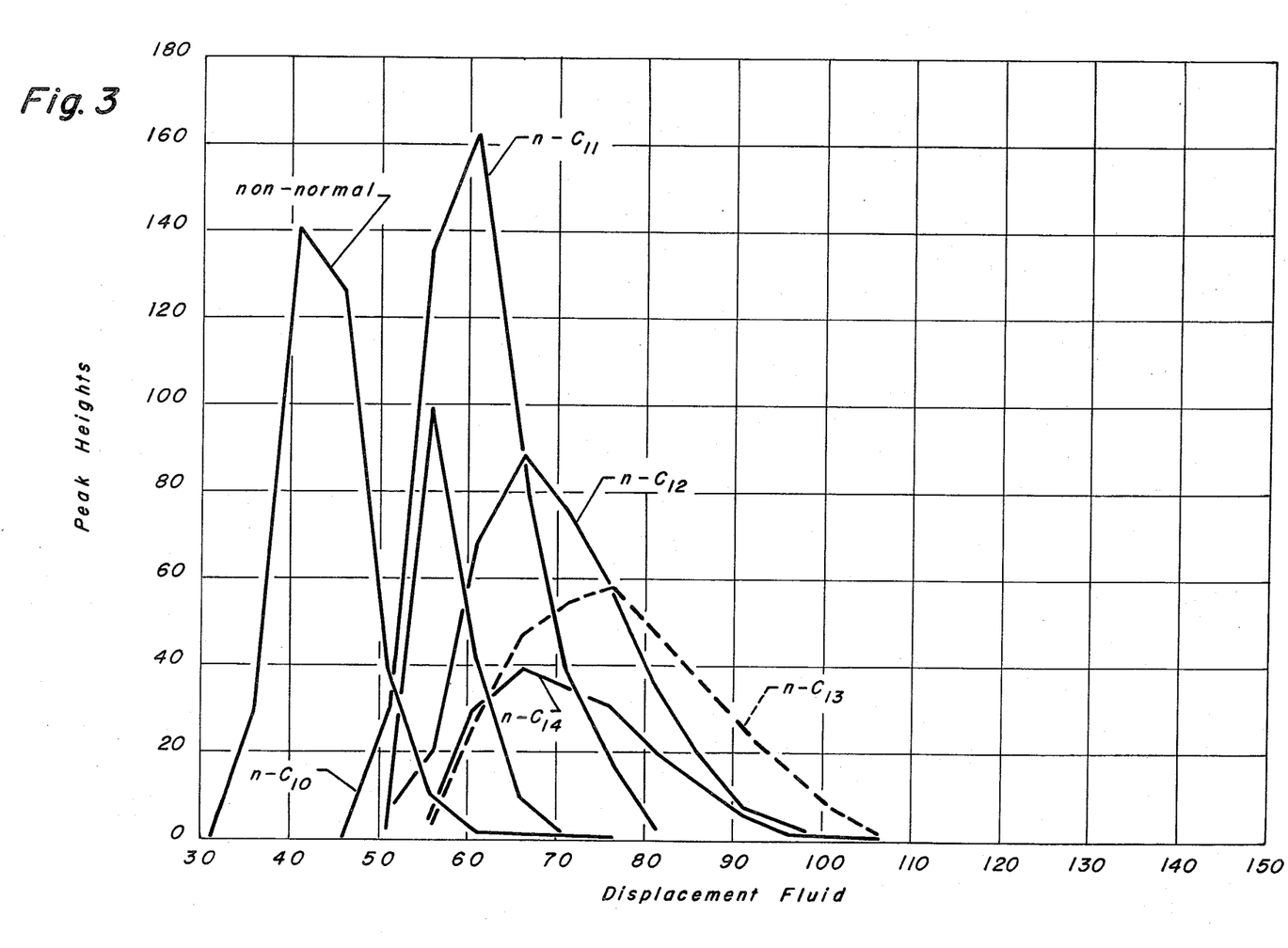
Figure 4:
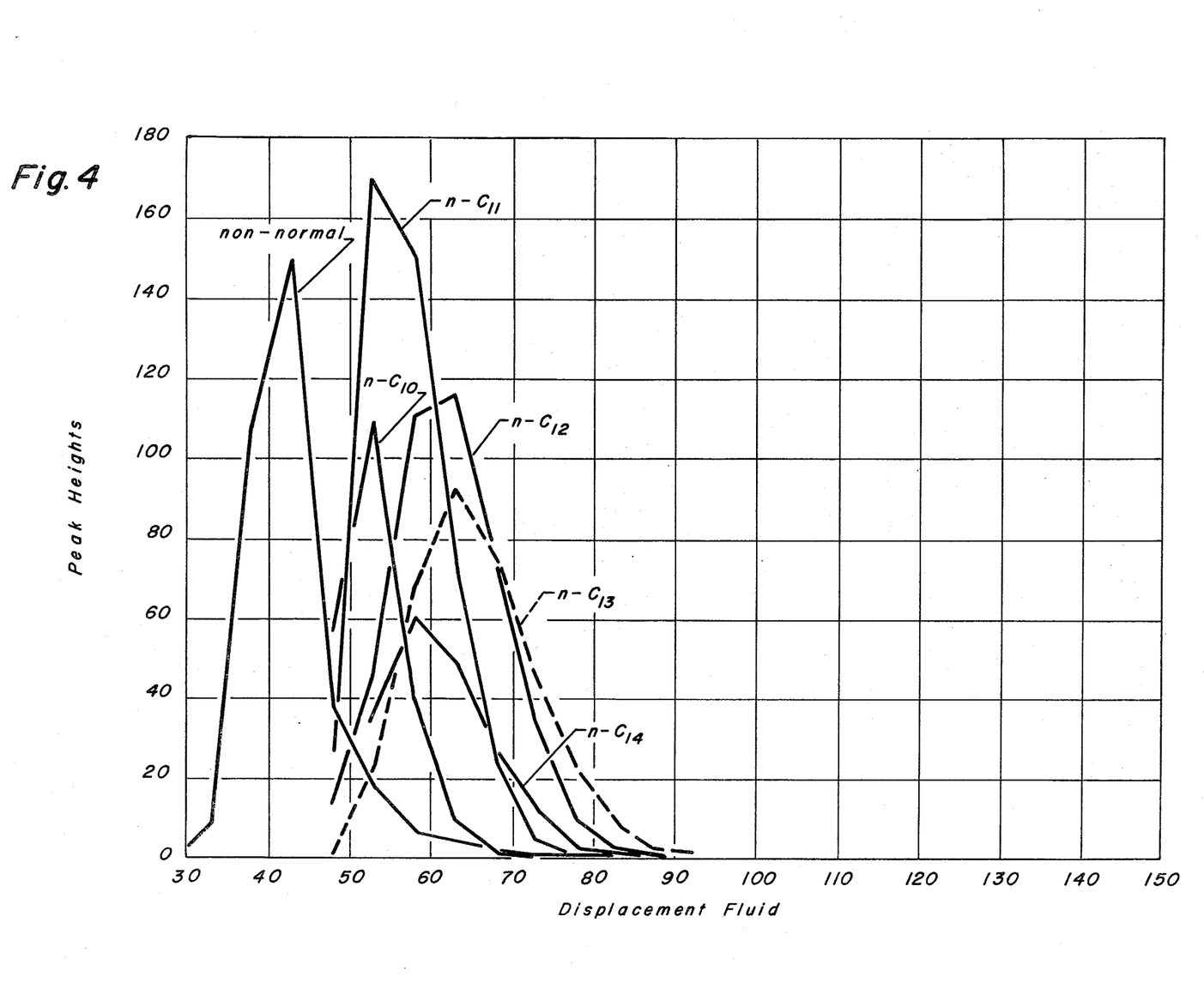
Figure 5:
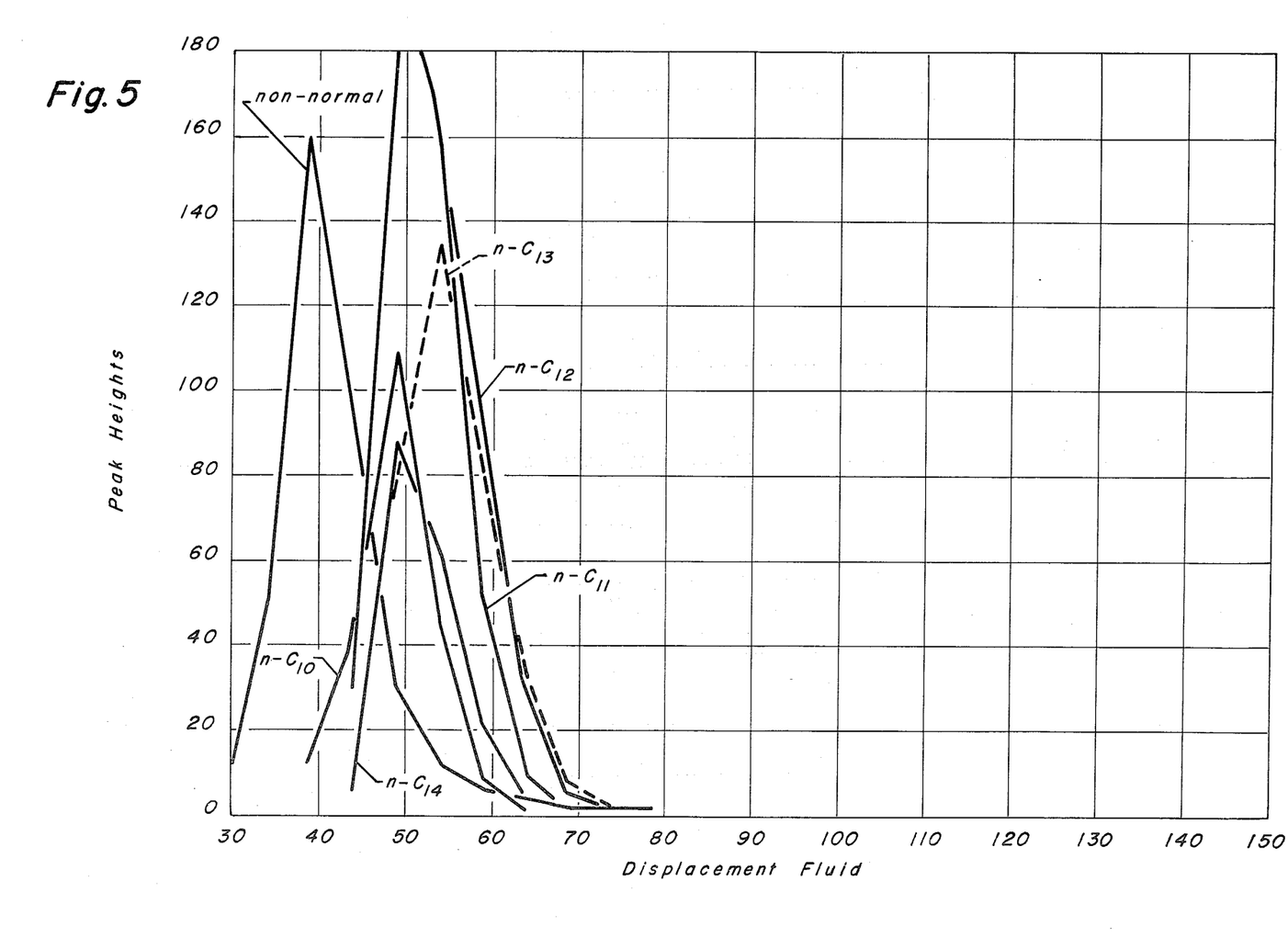

The above described pulse test apparatus was used to obtain data for this example. A series of five runs were made, with the differences between runs consisting of differences in the column temperature. The column was packed with alumina bound silicalite (80 wt. % silicalite). For each run, the flow was up the column at a rate between about 1.2 ml/min and 1.3 ml/min. The feed for each run comprised 11 LV% aromatics other than benzene, 66 LV% branched chain and cyclic hydrocarbons and 22% normal hydrocarbons with the normal and non-normal hydrocarbons having similar or overlapping molecular weight and boiling point distributions. The displacement material was a mixture of normal and iso-octane in a liquid volume ratio of 75:25, respectively. The feed was charged to the column in mixture with displacement fluid in a liquid volume ratio of 30:70, respectively. The respective molecular sieve-feed stream contacting temperatures for runs 1, 2, 3, 4 and 5 were 100° C., 120° C., 140° C., 160° C. and 185° C. The elution curves for each run are shown in correspondingly numbered FIGS. 1, 2, 3, 4 and 5.

The figures clearly show the advantage of the contacting temperature range of the present invention. All of the curves show a separation between the normal and non-normal components, however, at temperatures below about 120° C. the rates of elution (inverse to the quantity of displacement fluid required) are unduly slow (with significant tailing) and unacceptable for commercial application. On the other hand, at contacting temperatures above about 140° C. the rates of elution are far too high for commercial utility with the curves becoming so foreshortened at the highest temperature that little or no separation is realized.

What is claimed is:

1. A process for separating a normal $C_{17}$ or lighter paraffin hydrocarbon from a mixture of the same with another structural class of hydrocarbon selected from cyclic hydrocarbons other than benzene and branched chain paraffin hydrocarbons, which comprises contacting said mixture at a temperature of from about 120° C. to about 140° C. with zeolite free molecular sieve comprising silicalite to effect the selective retention of said normal hydrocarbon by said molecular sieve.

2. The process of claim 1 wherein said normal paraffin hydrocarbon is recovered by displacement with a displacement material at a temperature of from about 120° C. to about 140° C. and a pressure sufficient to maintain liquid phase.

3. The process of claim 2 wherein said displacement material comprises a normal hydrocarbon having a boiling point at least about 5° C. different than the boiling point of the normal hydrocarbon being separated.

4. The process of claim 3 wherein said displacement material comprises a mixture of iso-octane and normal hydrocarbon.

5. The process of claim 4 wherein said displacement material comprises a mixture of iso-octane and normal olefin.

6. The process of claim 1 wherein said contacting occurs at a pressure sufficient to maintain liquid phase.

7. A process for separating a normal paraffin hydrocarbon from a mixture of the same with a cyclic hydrocarbon other than the benzene, or branched chain paraffin hydrocarbon, which process employs a zeolite free molecular sieve comprising silicalite, which process comprises the steps of:

(a) maintaining net fluid flow through a column of said molecular sieve in a single direction, which column contains at least three zones having separate operational functions occurring therein and being serially interconnected with the terminal zones of said column connected to provide a continuous connection of said zones;

(b) maintaining a retention zone in said column, said zone defined by the molecular sieve located between a feed input stream at an upstream boundary of said zone and a raffinate output stream at a downstream boundary of said zone;

(c) maintaining a purification zone immediately upstream from said retention zone, said purification zone defined by the molecular sieve located between an extract output stream at an upstream boundary of said purification zone and said feed input stream at a downstream boundary of said purification zone;

(d) maintaining a displacement zone immediately upstream from said purification zone, said displacement zone defined by the molecular sieve located between a desorbent input stream at an upstream boundary of said zone and said extract output stream at a downstream boundary of said zone;

(e) passing said feed mixture into said retention zone at a temperature of from about 120° C. to about 140° C. and a pressure sufficient to maintain liquid phase to effect the selective retention of said normal paraffin hydrocarbon by said molecular sieve in said retention zone and withdrawing a raffinate output stream from said retention zone;

(f) passing a displacement material into said displacement zone at a temperature of from about 120° C. to about 140° C. and a pressure sufficient to maintain liquid phase to effect the displacement of said normal hydrocarbon from the molecular sieve in said displacement zone;

(g) withdrawing an extract output stream comprising said normal paraffin hydrocarbon and displacement material from said displacement zone;

(h) withdrawing a raffinate output stream comprising said branched chain paraffin hydrocarbon or cyclic hydrocarbons from said displacement zone; and (i) periodically advancing through said column of molecular sieve in a downstream direction with respect to a fluid flow in said retention zone the feed input stream, raffinate output stream, displacement fluid input stream, and extract output stream to effect the shifting of zones through said molecular sieve and the production of extract output and raffinate output streams.

8. The process of claim 7 wherein said displacement material comprises a hydrocarbon or mixture of hydrocarbons having a boiling point at least about 5° C. different than the boiling point of the $C_6$ hydrocarbon being separated.

9. The process of claim 8 wherein said displacement material comprises a mixture of iso-octane and normal hydrocarbon.

10. The process of claim 9 wherein said displacement material comprises a mixture of iso-octane and normal olefin.

11. The process of claim 7 further characterized in that it includes the step of maintaining a buffer zone immediately upstream from said displacement zone, said buffer zone defined as the molecular sieve located between the displacement fluid input stream at a downstream boundary of said buffer zone and a raffinate output stream at an upstream boundary of said buffer zone.

* * * * *